(12) United States Patent
McDonald

(10) Patent No.: US 6,206,887 B1
(45) Date of Patent: *Mar. 27, 2001

(54) OPTICAL LENS DEFORMATION AND INSERTION INTO THE EYE

(75) Inventor: Henry H. McDonald, Rancho Mirage, CA (US)

(73) Assignee: Surgical Concepts, Inc., Newport Beach, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/382,118

(22) Filed: Aug. 24, 1999

(51) Int. Cl.[7] ........................................................ A61F 9/00

(52) U.S. Cl. ............................................ 606/107; 623/6.11

(58) Field of Search ..................................... 606/107–206, 606/207, 205, 210; 623/6.11, 6.12, 6.19, 6.2, 6.21

(56) References Cited

U.S. PATENT DOCUMENTS

| 4,573,998 | * | 3/1986 | Mazzocco | 623/6.11 |
| 4,785,810 | * | 11/1988 | Baccala et al. | 606/107 |
| 4,813,957 | * | 3/1989 | McDonald | 623/6.11 |
| 4,959,070 | * | 9/1990 | McDonald | 623/6.11 |
| 5,549,614 | * | 8/1996 | Tunis | 606/107 |
| 5,562,676 | * | 10/1996 | Brady et al. | 606/107 |
| 5,766,182 | * | 6/1998 | McDonald | 606/107 |
| 5,919,197 | * | 7/1999 | Mcdonald | 606/107 |

\* cited by examiner

*Primary Examiner*—Pedro Philogene
(74) *Attorney, Agent, or Firm*—William W. Haefliger

(57) ABSTRACT

In apparatus for optical lens forming and displacing, the combination comprises body structure including lens deforming surfaces to receive a lens therebetween and to form the lens into multiple folds; multiple prongs to engage the lens folds; a plunger to displace the prongs endwise of and relative to surfaces and to discharge the folded lens endwise from the structure; and the structure including guide surfaces to cam the prongs toward one another to reduce the lens cross-section being displaced from the structure.

32 Claims, 3 Drawing Sheets

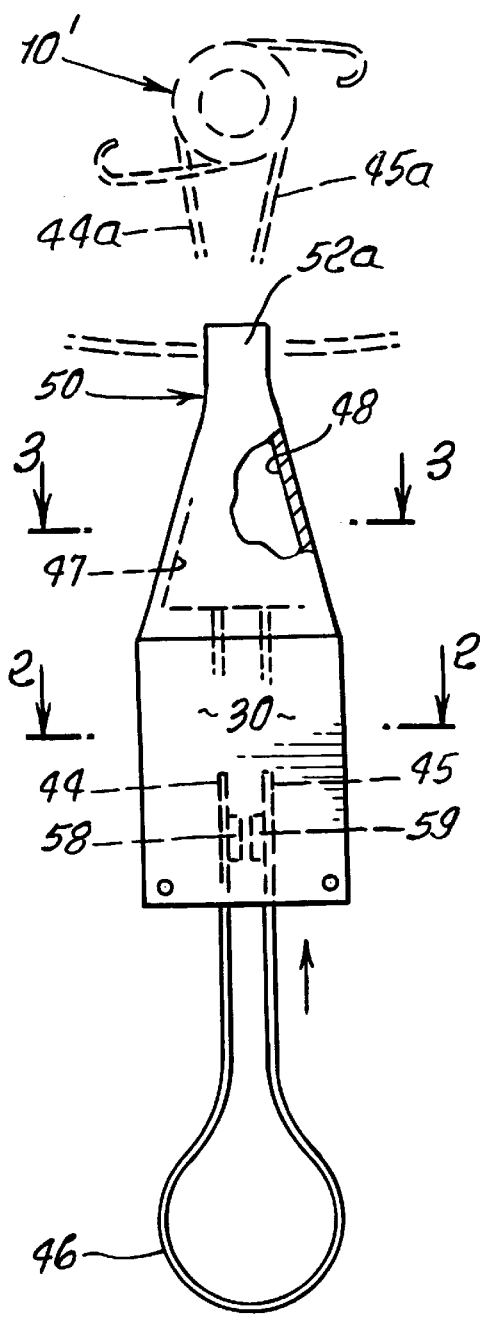
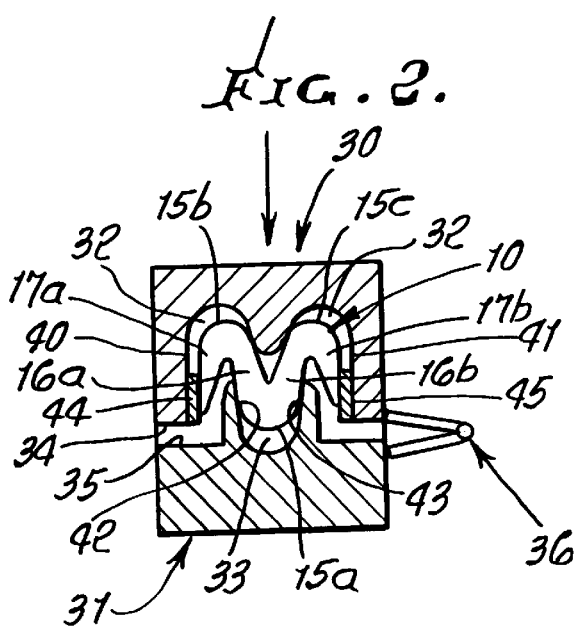
FIG. 1.
FIG. 2.

OPTICAL LENS DEFORMATION AND INSERTION INTO THE EYE

BACKGROUND OF THE INVENTION

This invention relates generally to insertion of an artificial lens unit into the eye; and more particularly to creation of a multi-folded lens unit, and insertion into a very small wound opening in the eye by use of a plunger, and controlled release of the lens unit in the eye, whereby very rapid lens replacement surgery can be achieved, with minimum disruption of the eye.

There is constant need for improvements in eye surgery, particularly in lens implant surgery, to achieve faster and more efficient lens insertion and positioning, as well as reduced size eye wound openings in the interests of faster healing. There is particular need in these regards, for implants in intraocular lens implant surgery.

Prior techniques are believed not to incorporate or suggest the unusual improvements in method and apparatus which are the subject of the present invention.

SUMMARY OF THE INVENTION

It is a major object of the invention to provide method and apparatus meeting the above needs, and providing for faster, more efficient, and less disruptive lens implant surgery.

Basically, the present method includes the steps:

a) providing structure including lens deforming surfaces to receive a lens therebetween and to form the lens into multiple folds, b) providing multiple prongs to engage the lens folds, c) providing and operating plunger means to displace the prongs endwise of and relative to the deforming surfaces and to discharge the folded lens endwise from the structure, d) the structure providing guide surfaces to cam the prongs toward one another to reduce the lens cross-section being displaced from the structure.

As will appear, it is another object to impart to the lens an M-shape having two laterally spaced legs interconnected by a U-shaped portion, to be displaced by the plunger; and to provide prongs configured for laterally deflecting the legs toward and into compacting relation with the U-shaped portion, in response to forward displacement of the lens by the plunger.

Such forming of the lens into folds typically includes folding the lens at loci proximate the interconnection of the legs with the U-shaped portion, and also at a locus proximate a crest defined by the U-shaped portion. Also, such deflecting of the legs typically includes displacing them toward a crest defined by the U-shaped portion, both initially, and also in response to forward displacement of the lens effected by the plunger.

A further object includes causing forward ends of the two prongs to spread apart to release the lens, in the eye; and an additional object is to provide hand manipulable structure and squeezing that structure to cause forward ends of the prongs to spread apart. Such spread-apart is typically accompanied by rocking of portions of the prongs that are displaced into close side-by-side relation, as will appear.

Yet another object is to provide initially deforming structure for the lens to include two bodies defining lens receiving cavities, said deforming surfaces located in those cavities, such bodies being relatively closable toward one another to initially deform the lens therebetween.

An additional object is to provide guide surfaces terminating at a lens discharge opening, and displacing said prongs to a lens release position in which the prongs extend through said lens discharge opening; further, at least one of said prongs is a pusher located to push the lens toward the guide surfaces which are convergent; and yet further, two of the prongs are positioned to sidewardly deflect and grip the lens therebetween.

An additional object is to provide for release of lens unit grasping by the prongs after the lens or lens unit has been inserted endwise into the eye, whereby completed unfolding of the unit folds at its opposite ends precedes completed unfolding of the folds at the medial location. In this regard, the lens unit grasping prongs are provided to have lens unit pinching surfaces located to pinch the folded unit to greater extent at a location medially of the unit than at locations proximate its opposite ends. Such surfaces of the grasping prongs typically have convex extents presented oppositely, toward opposite side folds of the folded unit.

Release of such a medially pinched lens thereby proceeds gradually, instead of explosively. accompanied by prong spreading with the medially pinched portion of the lens unit completing its unfolding after completion of unfolding of lens unit opposite ends, thereby minimizing potential impact damage to the eye structure.

A yet further object is to insert the multi-folded lens into the eye zone between the iris and cornea of the eye, via very small eye wound opening, such as about 2 mm., so that unfolding will not damage the natural lens or its surface. Subsequently, and after completion of lens unit unfolding, as from M shape, the reshaped lens unit may be manipulated, a portion at a time, into the intraocular zone between the iris and the natural lens, for ultimate, safe placement adjacent the natural lens surface.

Additional objects include provision of apparatus or tools to accomplish multiple folding of a very small plastic lens unit, and its positioning in the eye, for safe unfolding, as referred to. As will appear, such apparatus typically includes elements to form at least three folds, and an M-shaped folded lens may be formed, and displaced, as referred to.

These and other objects and advantages of the invention, as well as the details of an illustrative embodiment, will be more fully understood from the following specification and drawings, in which:

DRAWING DESCRIPTION

FIG. 1 is a plan view of lens sidewise folding, and endwise displacing elements, as referred to;

FIGS. 2 and 3 are sections taken on lines 2—2 and 3—3, respectively, in FIG. 1;

FIG. 3*a* shows a completely compressed lens cross-section, at the time of insertion into a slit in the eye;

DETAILED DESCRIPTION

Figure 8:
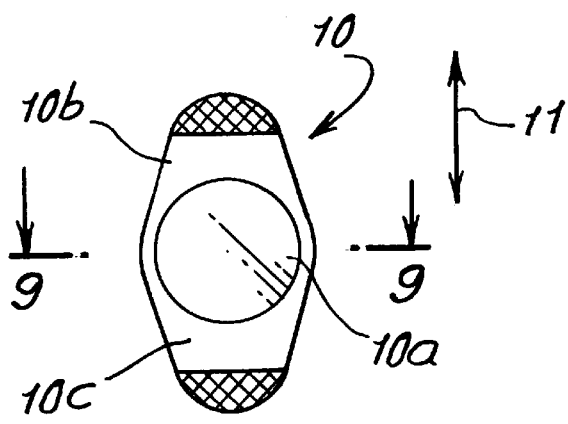
FIG. 8 is a plan view of a lens or lens unit about to be folded.
Figure 9:
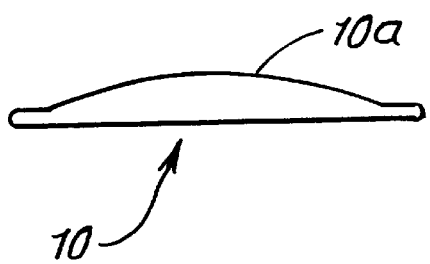
FIG. 9 is a section taken on lines 9—9 of FIG. 8.

In FIGS. 8 and 9, a plastic lens unit 10 has a central, generally circular, relatively thicker, lens zone 10*a*, and two tabular haptics 10b and 10c. If desired, the haptics may be filamentary as seen in FIG. 1, at lens 10'. The unit is elongated in direction 11, and its thickness decreases as shown at the haptics. The lens unit may typically be sized and constructed for insertion into the inter-ocular zone of the eye, between the cornea and natural lens, to be allowed to controllably unfold, as in the sub-zone between the iris and the cornea, i.e., spaced from the natural lens for maximum protection of the natural lens, during unfolding. Examples of lens material are collamer and silicone resin. Folding elements are provided herein for folding the lens unit at multiple locations, to form at least three folds, such as accordian folds, to compact the lens for insertion into the eye via a very small slit in the eye wall.

In FIG. 2, the parallel fold bend locations are seen at 15a–15c, in alignment with the fold forming parallel elements, to be described. The folded lens includes a U-shaped portion having segments 16a and 16b extending upwardly from 15a, and legs 17a and 17b extending downwardly from 15b and 15c, and deflected toward segments 16a and 16b, to compact the lens for insertion into the eye.

Two bodies 30 and 31 are provided to define lens receiving cavities 32 and 33, and lens deforming surfaces are provided on the bodies to deform the lens into M-shape as the bodies are relatively closed toward one another (for example, body 30 lowered onto body 31, to interengage at shoulders 34 and 35). The bodies may have guided (such as hinged) interconnection (as at 36) or guide pins can be used. Lens deforming surfaces are provided at 40–43.

Figure 3:
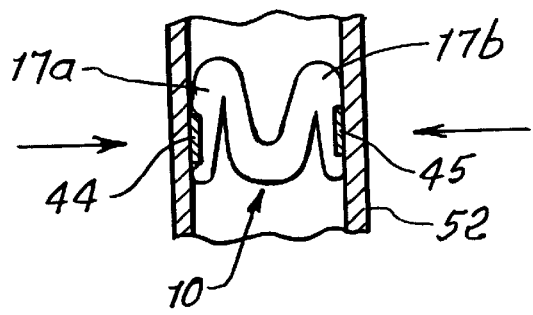
Figure 3A:
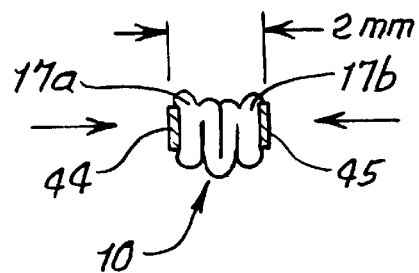
Figure 7:
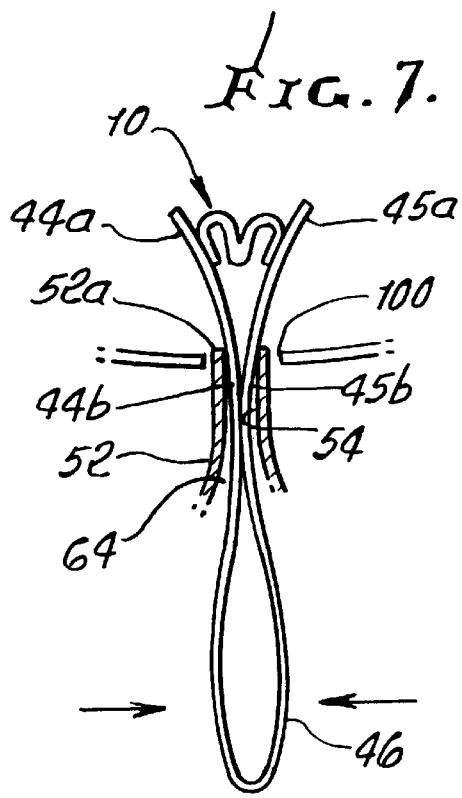
FIG. 7 is a view like FIG. 6, but showing the ends of the displaced prongs having spread apart due to camming engagement of rocking portions of the prongs with insertion structure.

Multiple elongated prongs are provided to engage the outer sides of the lens folds, such as legs 17a and 17b, two such prongs being shown at 44 and 45. The prongs are typically interconnected via a bow spring 46. As the prongs are moved forwardly, in response to forward advancement of 46, the prongs 44 and 45 are progressively deflected toward one another, as by cam surfaces 47 and 48 provided in a body forward portion 50, for squeezing the M-shaped lens into very compact form, as seen in FIGS. 1, 3 and 3a, the latter FIG. 3a showing the lens in compacted form ready to be inserted into the eye, as via a small slit or wound 100 (see FIG. 7) of about 2–3 mm. length. After the lens is inserted, the metallic prong forward extents 44a and 45a, forward of the tip end 52a of the forwardly tapered compression body extent 52, tend to progressively separate as seen in FIG. 7, aiding non-expansive release of the folded lens. The prongs typically may interengage and rock at zones 44b and 45b, within the narrowly constricted zone 54 of the body extent 52, due to compression of the spring handle 46, for example as seen in FIG. 7.

Figure 4:
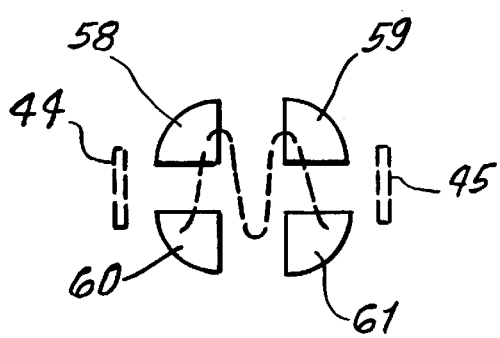
FIG. 4 is an enlarged cross-section taken through relatively expanded springs.
Figure 5:
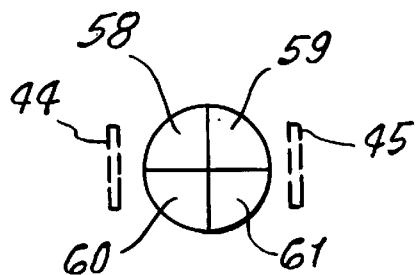
FIG. 5 is a view like FIG. 4, but showing the prongs after their collapse toward one another, during lens endwise displacement.
Figure 6:
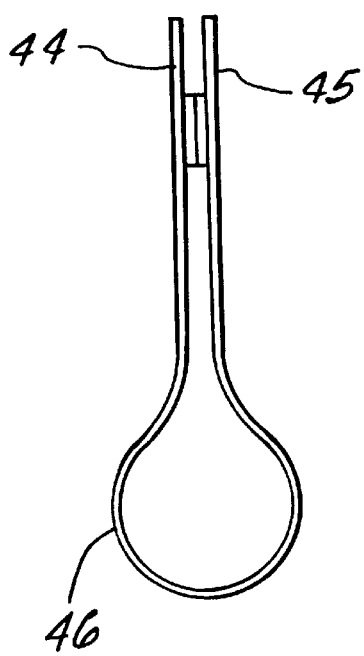
FIG. 6 is a view of prong displacement apparatus.

Plunger means or structure is also provided to displace the prongs endwise of and relative to said surfaces and to discharge the folded lens endwise from said structure. See for example the plunger parts indicated at 58–61 in FIGS. 1, 4 and 5. The forward ends of the plunger parts engage and push the folded lens forwardly, during its forward advancement and during progressive constriction in the tapered hollow body forward extent 52, and toward body tip 52a, from which the lens is carried forward into the eye, as the prong forward extents 44a and 44b expand. The narrowing of the passage 64 in 52 tends to constrict the plunger parts, for example from their expanded condition seen in FIG. 4, to their constricted condition seen in FIG. 5. Accordingly, all that is needed to insert a lens is its initial folding as in the cavities 32 and 33 in bodies 30 and 31, and subsequent forward advancement by the plunger to effect folded lens constriction and expelling into the eye, with no prong manipulation by a surgeon being required, other than forward pushing of 46, and controlled squeezing of 46 to control separation of prong forwardmost extents 44a and 44b.

Body 52 may be carried by one or both of 30 and 31, and may be integral with one or both of same.

It will also be understood that the invention enables simultaneous shaping and controlled maintenance of an intraocular multi-faced lens implant, as by controlled unfolding during passage into the anterior chamber of the eye. This may typically occur as the leading haptic passes into the posterior ocular chamber.

I claim:

1. In apparatus for optical lens forming and displacing, the combination comprising:
   a) body structure including lens deforming surfaces to receive a lens therebetween and to form the lens into multiple folds,
   b) multiple prongs to engage the lens folds,
   c) plunger means to displace the prongs endwise of and relative to said surfaces and to discharge the folded lens endwise from said structure,
   d) said structure including guide surfaces to cam the prongs toward one another to reduce the lens cross-section being displaced from said structure.

2. The combination of claim 1 wherein said structure includes two bodies defining lens receiving cavities, said surfaces located in said cavities.

3. The combination of claim 2 wherein said bodies have hinged interconnection.

4. The combination of claim 2 wherein said plunger means is located endwise of said cavities.

5. The combination of claim 1 wherein said guide surfaces taper endwise of said surfaces.

6. The combination of claim 5 wherein said guide surfaces terminate at a lens discharge opening, and said prongs have a lens release position in which the prongs extend through said lens discharge opening.

7. The combination of claim 1 including said lens folded between said surfaces.

8. The combination of claim 7 wherein the lens has M shape.

9. The combination of claim 7 wherein at least one of said prongs is located to push the lens toward said guide surfaces.

10. The combination of claim 7 wherein two said prongs are positioned to sidewardly deflect and grip the lens therebetween.

11. The combination of claim 9 wherein two of said prongs are positioned to sidewardly deflect and grip the lens therebetween.

12. The combination of claim 1 wherein the prongs have intermediate portions with rocking interengagement.

13. In the method of optical lens forming and displacing, the steps that include:
   a) providing structure including lens deforming surfaces to receive a lens therebetween and to form the lens into multiple folds,
   b) said structure including multiple prongs to engage the lens folds,
   c) providing and operating plunger means to displace the prongs endwise of and relative to said surfaces to discharge the folded lens endwise from said structure,
   d) said structure provided with guide surfaces to cam the prongs toward one another to reduce the lens cross-section being displaced from said structure.

14. The method of claim 13 including providing said structure to include two bodies defining lens receiving cavities, said surfaces located in said cavities.

15. The method of claim 14 including providing a guided interconnection between said bodies, and displacing said bodies to deform the lens therebetween.

16. The method of claim 14 including locating said plunger means endwise of said cavities.

17. The method of claim 13 providing said guide surfaces to have taper endwise of said surfaces.

18. The method of claim 17 wherein said guide surfaces terminate at a lens discharge opening, and displacing said prongs to a lens release position in which the prongs extend through said lens discharge opening.

19. The method of claim 13 including said lens is folded between said surfaces.

20. The method of claim 19 wherein the lens is formed to have M shape.

21. The method of claim 19 wherein at least one of said prongs is a pusher located to push the lens toward said guide surfaces.

22. The method of claim 19 wherein two of said prongs are positioned to sidewardly deflect and grip the lens therebetween.

23. The method of claim 21 wherein two of said prongs are positioned to sidewardly deflect and grip the lens therebetween.

24. The method of claim 23 including causing forward ends of said two prongs to spread apart to release the lens, in the eye.

25. The method of claim 24 including providing hand manipulable structure and squeezing said structure to cause said forward ends of the prongs to spread apart.

26. The method of deforming a flexible artificial lens, preparatory to insertion into the eye, the lens having a peripheral edge, that includes the steps:

a) advancing the lens edgewise in a longitudinal direction, b) and progressively compacting the lens in a lateral direction, during said advancing.

27. The method of claim 26 wherein said compacting includes exerting lateral force or forces on the lens to progressively compact the lens in folded condition.

28. The method of claim 27 wherein the lens is progressively compacted in an M-folded condition, during said advancing.

29. The method of claim 27 wherein said compacting includes exerting camming force or forces transmitted laterally to the lens in response to said longitudinal advancement of the lens.

30. The method of claim 29 including providing a lens camming surface or surfaces to exert said camming force or forces, and displacing the lens longitudinally in adjacency to said surface or surfaces to effect said camming force exerting.

31. The method of claim 29 including providing a prong or prongs advancing with the lens, and adjacent the advancing lens, said lateral force being transmitted to the lens via the prong or prongs, during said advancement.

32. The method of claim 31 including manipulating said prong or prongs to release the lens within the eye.

* * * * *